United States Patent [19]
Weissleder et al.

[11] Patent Number: 5,514,379
[45] Date of Patent: May 7, 1996

[54] HYDROGEL COMPOSITIONS AND METHODS OF USE

[75] Inventors: Ralph Weissleder, Charlestown; Alexei Bogdanov, Newton, both of Mass.

[73] Assignee: The General Hospital Corporation, Boston, Mass.

[21] Appl. No.: 927,068

[22] Filed: Aug. 7, 1992

[51] Int. Cl.$^6$ .......................... A61K 9/10; A61K 49/00; A61K 49/04
[52] U.S. Cl. .................. 424/426; 424/486; 424/488; 424/484; 252/315.1; 252/315.3; 514/944
[58] Field of Search ................... 424/426, 484, 424/2, 4, 5; 252/315.1; 525/55.1, 937; 530/810, 816, 817, 402; 514/944, 773–776

[56] References Cited

U.S. PATENT DOCUMENTS

| | | | |
|---|---|---|---|
| 4,113,785 | 9/1978 | Helfert et al. | 260/615 B |
| 4,124,705 | 11/1978 | Rothman et al. | 424/180 |
| 4,126,669 | 11/1978 | Rothman et al. | 424/1 |
| 4,684,558 | 8/1987 | Keusch et al. | 428/40 |
| 4,814,098 | 3/1989 | Inada et al. | 252/62.51 |
| 4,865,846 | 9/1989 | Kaufman | 424/428 |
| 4,976,703 | 12/1990 | Franetzki et al. | 604/247 |
| 4,986,980 | 1/1991 | Jacobsen | 424/9 |
| 5,008,109 | 4/1991 | Tin | 514/944 |
| 5,032,391 | 7/1991 | Helioff et al. | 514/944 |
| 5,041,292 | 8/1991 | Feijen | 424/484 |
| 5,208,324 | 5/1993 | Klaveness et al. | 536/17.1 |

FOREIGN PATENT DOCUMENTS

| | | |
|---|---|---|
| 0046136 | 2/1982 | European Pat. Off. . |
| 0260098 | 3/1988 | European Pat. Off. . |
| WO89/11874 | 12/1989 | WIPO . |
| WO91/15753 | 10/1991 | WIPO . |

OTHER PUBLICATIONS

Bischoff et al., *Urol. Int.*, 32:323–335 (1977).
Bligh et al., *Magn. Reson. Med.*, 17:516–532 (1991).
Chazov et al., *Thromb. Res.*, 12:809–816 (1978).
Durand et al., Chapter 21 of Selected papers from Networks '88, 9th Polymer Network Group Meeting, Freiburg, West Germany, 26–30 Sep. 1988 pp. 283–301, W. Burchard and S. B. Ross–Murphy editors.
Krejcarek et al., *Biochem. Biophys. Res. Comm.*, 77:581–586 (1977).
Fujimoto et al., *Cancer*, 56:2404–2410 (1985).
Hnatowich et al., *J. Immunol. Meth.*, 65:147–157 (1983).
Jayakrishnan et al. *J. Biomed. Mat. Res.*, 25:993–1004 (1990).
Kennedy et al., *Am. Surg.*, 33:763–771 (1967).
Larsen et al., *J. Biomed. Mater. Res.*, 25:699–710 (1991).
Link et al., *Acta Radiol.*, 6:727–729 (1988).
Mitsuhashi et al., *Am. J. Path.*, 124:246–52 (1986).
Rao et al., *J. Neuroradiol.*, 18:61–69 (1991).
Shelub et al., *J. Appl. Physiol.*, 56:810–15 (1984).
Szmigielski et al., *Pol. Przeg. Rad.*, 47:387–90 (1983).
Torchilin et al., *J. Biomed. Mater. Res.*, 11:223–234 (1977).
Torchilin et al., *J. Biom. Mater. Res.*, 19:461–466 (1985).
Verdon et al., *Scan. Micro.*, 4:341–350 (1990).
Weyne et al., *Stroke*, 18:128–37 (1987).
Winding, O., *Neuroradiol.*, 21:123–126 (1981).
Wright et al., *Radiology*, 142:351–54 (1982).
Gore et al., *Magn. Reson. Med.*, 9:325–332 (1989).

*Primary Examiner*—Edward J. Webman
*Attorney, Agent, or Firm*—Fish & Richardson

[57] ABSTRACT

Biocompatible, biodegradable, hydrogels are prepared from a backbone bonded to a cross-linking agent. Suitable backbones include proteins and polysaccharides, e.g., albumin, polymannuronic acid, or polygalacturonic acid. Suitable cross-linking agents include polyvalent derivatives of polyethylene or polyalkylene glycol. These hydrogel compositions may be loaded with diagnostic labels, e.g., radiopaque, paramagnetic, or superparamagnetic materials, or therapeutic drugs, e.g., chemotherapeutic drugs, antibiotics, or cells that produce therapeutic agents. This invention also relates to methods of use of such hydrogels for imaging during interventional procedures of a patient.

17 Claims, 6 Drawing Sheets

HYDROGEL COMPOSITIONS AND METHODS OF USE

This invention was made with Government support under Contract #RO1-CA-54886 awarded by the National Institutes of Health. The Government has certain rights in the invention.

BACKGROUND OF THE INVENTION

This invention relates to biocompatible and biodegradable hydrogel compositions, and to methods of use of such hydrogels for imaging during interventional procedures of a patient.

A variety of radiologic imaging techniques are available that allow the operator to diagnose disease and monitor therapeutic interventional procedures such as embolizations or abscess drainages. Whereas many imaging techniques are useful for the diagnosis of disease, e.g., ultrasound, scintigraphy, positron emission tomography ("PET"), single photon emission computed tomography ("SPECT"), X-ray, computed tomography ("CT"), and magnetic resonance imaging ("MRI"), only X-ray (fluoroscopy, computed tomography) and MRI are frequently used to monitor therapeutic interventions.

Therapeutic interventional imaging procedures are performed primarily in the fields of interventional radiology ("IR") and minimal invasive therapy ("MIT"). Both fields have become important adjuncts to traditional surgical techniques and have even replaced some classical surgical techniques because of their lower invasiveness, shorter convalescence, and similar or equal effectiveness. Well established IR procedures include abscess drainage, tumor embolizations, and biopsies. IR procedures are always performed in conjunction with radiological imaging, whereas MIT procedures are more surgical in nature and use imaging only when it is necessary to visualize the interventional devices used during the procedure.

Therapeutic drugs are often used in conjunction with procedures such as MIT and IR, and the concentration of these drugs in a patient is indicative of the efficiency of treatment. Therefore, it is important to accurately monitor the delivery, concentrations, and release, of these drugs in vivo, particularly after MIT, IR, and surgery. However, such drugs are typically not detectable by conventional CT or MR imaging techniques, because they do not contain radiopaque or magnetically active labels ("contrast agents").

Contrast agents were originally developed for use with diagnostic imaging techniques to further improve the diagnosis of disease. However, these agents have no therapeutic effect in interventional imaging procedures. For example, CT and MR contrast agents designed for intravascular use are water-soluble and are usually small molecules containing radiopaque, paramagnetic, or superparamagnetic elements. Such contrast agents are primarily administered intravascularly to facilitate diagnosis by selectively altering the signal arising in normal or abnormal tissues. Certain contrast agents also include particulate materials for gastrointestinal (oral or rectal) use. However, these gastrointestinal agents are undesirable for interventional use, because they are hyper-osmolar and/or toxic if administered intravascularly or intracorporally.

Known diagnostic agents for human use, e.g., contrast agents for X-ray imaging, contain labels, e.g., iodine or barium, which are covalently or non-covalently bonded to other atoms to make them biocompatible. Diagnostic MR contrast agents usually contain a paramagnetic label, e.g., gadolinium ("Gd"), dysprosium, iron, or manganese, or a superparamagnetic label, e.g., iron oxide. These otherwise toxic labels are made biocompatible by chelating the ions, e.g., with diethylenetriamine-pentaacetic acid ("DTPA") to form Gd-DTPA, or by coating particulates with a polymer, e.g., with dextran or arabino-galactan, to form iron oxides.

For example, Hall, PCT patent application 89/11874 (1990), describes contrast preparations containing a biodegradable, porous particulate substrate, e.g., Sepharose™ or polystyrene, with surface bound paramagnetic labels, e.g., Gd-DTPA, with no significant release of the label when administered. The substrate may be a hydrogel, polyglycolic acid, cross-linked protein, and the like. These water-insoluble preparations may be used as MR contrast agents, e.g., for the gastrointestinal tract or the vascular system.

Bligh et al., *Magn. Reson. Med.*, 17:516–532 (1991), describes the use of soluble (e.g., dextran) and insoluble (e.g., starch or cellulose) polysaccharide-linked Gd-DTPA contrast agents for MR imaging. The insoluble polysaccharides are not covalently linked to each other by a cross-linking reagent. Soluble agents were administered intravenously and insoluble agents were fed orally without injections into the blood stream.

Unger, PCT patent application 91/15713 (1991), describes aqueous solutions of polymers as contrast media for MRI. These media comprise biocompatible polymers, e.g., polyethylene glycols, polyoxyethylene glycols, or polymers of galacturonic or mannuronic acid, in admixture (not covalently bound) with, e.g., paramagnetic or superparamagnetic agents. If cross-linked, these contrast media may be water-insoluble.

In addition, Gd-DTPA labeled gel "tissue phantoms," i.e., artificial in vitro models of tissues, made of polyacrylamide, agarose, glutaraldehyde cross-linked albumin gels, or styrenes, have been described for experimental MR imaging or other uses such as magnetic separations. However, these agents are not desirable or suitable for human use because of their local or systemic toxicity.

Inada et al., U.S. Pat. No. 4,814,098, describes the use of a ferromagnetic material bound to a physiologically active substance, e.g., an enzyme, through a PEG derivative linker. These water-soluble colloidal solutions are used for magnetic separation of physiologically active substances.

Some radiopaque particulate materials have also been proposed for embolization purposes. These materials exhibit a strong local toxic reaction, and may elicit an immunogenic response upon repeated administration or may not be biodegradable. Furthermore, these agents do not contain paramagnetic labels and are unlikely to be useful for drug delivery estimation because of the large quantities of radiopaque materials required for CT, e.g., 10 to 40 percent of the particulate is iodine.

For example, radiopaque hylan for embolization contains a combination of hylan, e.g., hyaluronan or hyaluronate (cross-linked with vinyl-sulfone), tantalum, microscrystalline cellulose, hexamethonium chlorine, and thrombin. Additional embolization materials include radiopaque non-biodegradable hydrogel microspheres based on poly (2-hydroxyethyl) methacrylate ("PHEMA")/iothalamic or iopanoic acid as described by Jayakrishnan et al., *J. Biomed. Mat. Res.*, 25:993–1004 (1990). These microspheres were non-biodegradable over 6 month interval when implanted into rats.

Other embolization materials include Sephadex™ and Sepharose™, which are polysaccharides cross-linked with halogenated compounds such as epichlorohydrin. A method for obtaining biodegradable Sephadex, e.g., partially oxidized Sephadex, is described in Torchilin et al., *J. Biomed. Mater. Res.*, (1977). Sephadex microparticles have also been labelled with ferromagnetic iron oxide and used for immobilizing enzymes and targeting the microparticles by applying an external magnet.

Certain hydrogels and microspheres have also been used for drug delivery. For example, biodegradable polymer systems have been described for the slow release of therapeutic drugs. Chemotherapeutic drugs have been bound to or incorporated into a variety of slow release systems including fibrinogen microspheres, albumin, gelatin, methylene diisocyanate cross-linked collagen, polylactic acid spheres, polysaccharides such as dextran and starch, or polyamino acids. All of these agents are expected to have high local tissue toxicity, be immunogenic in vivo, or be non-detectable by an imaging system.

For example, Feijen, U.S., Pat. No. 5,041,292, describes a biodegradable hydrogel for drug delivery systems which consists of proteins cross-linked with polysaccharides, e.g., heparin, heparan, or chondroitin, to form microspheres loaded with a drug using a solvent extraction technique.

SUMMARY OF THE INVENTION

The invention features biodegradable, biocompatible, hydrogels for imaging during interventional procedures, e.g., MIT and IR, to monitor and guide these procedures. These hydrogels are water-insoluble yet water-swellable, i.e., they can absorb water. This water absorption is beneficial for MR imaging of these compounds, because this imaging technique measures the relaxivities of the protons in the water.

These hydrogels include a polymeric backbone insolubilized by cross-linking agents which allow the hydrogels to absorb large amounts of water, which makes them well suited for proton relaxation imaging, e.g., MRI. The hydrogels also may be loaded with a diagnostic label detectable by CT or MR imaging techniques, and/or with a therapeutic drug, and are administered intravascularly as well as by implantation. The diagnostic labels and/or therapeutic drugs can be loaded into the hydrogel during synthesis, or afterwards, e.g., by diffusion into the hydrogel compositions.

The hydrogel compositions disclosed herein have high biocompatibility, e.g., they do not cause severe side effects, and low immunogenicity of both the primary materials and their degradation products, which allows repeated administration. In addition, these hydrogels when loaded with labels or drugs exhibit minimal or nonexistent local or systemic toxicity, compared to the potentially toxic labels or drugs with which they are loaded. At the same time, despite being cross-linked, these hydrogels are rapidly degraded in vivo, e.g., through enzymatic degradation, into non-toxic compounds within a few days to weeks.

The invention features a biocompatible, biodegradable, hydrogel including a backbone bonded to a cross-linking agent of the formula $R_1$—O—[(CH$_2$)$_n$—O]$_m$—$R_2$, wherein each $R_1$ and $R_2$, independently, is an organic group, at least one of $R_1$ and $R_2$ being capable of reacting with the backbone, n is 2 or 3, preferably 2, inclusive, and m is an integer from 10 to 200, and preferably from 50 to 150, inclusive. $R_1$ and $R_2$ may be the same or different.

These hydrogel compositions can be loaded with a reporter group, e.g., a diagnostic label or therapeutic drug, that may be entrapped in or covalently bonded to the hydrogel. Such labels are detectable by various imaging techniques, e.g., X-ray imaging (e.g., an iodine containing compound), which includes fluoroscopy and CT scanning, or magnetic resonance imaging (e.g., a gadolinium containing compound, e.g., Gd-DPTA).

The reporter group may also be a cell, or cell line, loaded into the hydrogel where the cell can grow and produce a therapeutic agent, e.g., an anti-cancer agent, antibiotic, cardiovascular agent, analgesic, central nervous system-active agent, hematopoietic agent, hemostasis agent, hormone, pro-hormone, protein, or an enzyme.

When the backbone includes a proteinaceous macromolecule, it includes at least 5 percent, and preferably from 20 to 50 percent, by weight of the proteinaceous macromolecule of an initial protein solution. When the backbone includes a polysaccharide derivative, it includes at least 1 percent, and preferably from 2 to 5 percent, by weight of the polysaccharide derivative of an initial polysaccharide derivative solution. The backbone may also include a synthetic polymer.

The backbone may be a plasma protein, e.g., albumin, tissue protein, e.g., collagen, glycoprotein, recombinant protein, polyamino acid, e.g., polylysine, carboxylated polysaccharide, glycosaminoglycan, dextran derivative, starch derivative, polyethyleneimine, or polyethylene glycol derivative. The backbone is preferably albumin, polymannuronic acid, or polygalacturonic acid.

The cross-linking agent may be, e.g., a polyvalent derivative of polyalkylene glycol or polyoxyethylene glycol, and is preferably a derivative of polyethylene glycol, polypropylene glycol, or copolymers thereof.

The invention also features a method for preparing these hydrogels by reacting the backbone with the cross-linking agent to produce the hydrogel. Certain backbones may first be derivatized to make them reactive, or more reactive. The invention also features a method of loading the hydrogel with a reporter group, e.g., during or after synthesis of the hydrogel.

The invention further features a method for providing an image, e.g. X-ray or MR image, of an internal region of a patient by administering to the patient a diagnostically effective amount of a labeled hydrogel, and scanning the patient using an imaging technique that can detect the label to obtain an image of the region. A "diagnostically effective amount" of the hydrogel is an amount that will provide an image of the hydrogel in the patient.

The invention also features a method for diagnosing the presence of diseased tissue in a patient by administering to the patient a diagnostically effective amount of a labeled hydrogel, and scanning the patient using an imaging technique that can detect the label to obtain a visible image of any diseased tissue in the patient.

In addition, the invention features a method for treating diseased tissue, e.g., cancer, infection, deficiency states, or hemorrhage, in a patient by administering to the patient a therapeutically effective amount of a hydrogel loaded with a therapeutic drug, cell that produces a therapeutic drug, and/or label, and scanning the patient using an imaging technique that can detect the label to obtain a visible image of any diseased tissue in the patient. A "therapeutically effective amount" of the hydrogel is an amount that will provide a therapeutic benefit to the patient. The treatment is effected by the release of pro-drugs, therapeutic drugs, cells, proteins, etc. from the hydrogel or by the hydrogel physically interrupting blood flow after intravenous administration.

The invention also features a method for estimating the concentration of a drug delivered to a patient from a hydrogel loaded with a drug and/or a label, by administering a therapeutically effective amount of the hydrogel to the patient, scanning the patient using an imaging technique that can detect the label to obtain an image of the label, calculating the release rate of the label, determining a correlation between the label release rate and the concentration of the drug in the hydrogel, and estimating the concentration of the drug delivered to the patient based on the correlation.

The invention further features a method for embolizing a given region in a patient comprising injecting an effective amount of a hydrogel loaded with a label and/or a drug intravascularly into the region to be embolized. The embolized region then may be scanned using an imaging technique that can detect the label to obtain an image of the embolized region.

Furthermore, the invention features a method for delivering a drug to a patient over an extended period of time by administering a therapeutically effective amount of a hydrogel loaded with a drug, label, and/or cell to the patient.

The invention also features a method for providing an image of an interventional device in an internal region of a patient in real time by coating the device with a labeled hydrogel, using the device in an internal region in the patient, and scanning the patient using an imaging technique that can detect the label to obtain an image of the device. The invention also covers interventional devices coated with a labeled hydrogel.

The term "derivative" as used herein means a compound whose core structure is the same as or closely resembles that of a parent compound, but which has a chemical or physical modification, such as different or additional side groups; the term includes copolymers of parent compounds.

The term "loaded" when used herein to describe a hydrogel encompasses any form of incorporation (covalent or non-covalent) of the reporter group into the hydrogel of the invention. The reporter group may be entrapped within the hydrogel matrix or may be covalently bonded to either the backbone or the cross-linking agent of the hydrogel.

The term "reporter group" encompasses diagnostic labels, e.g., paramagnetic or superparamagnetic compounds such as Gd-DTPA or iron oxides, radiopaque compounds, such as iodine compounds; therapeutic drugs, such as antibiotics, hormones, anti-cancer compounds, cardiovascular agents, enzymes, analgesics, central nervous system-active drugs; and cells producing therapeutic agents, e.g., insulin.

The term "imaging" includes any technique that can diagnose disease in a human or animal patient. The term includes X-ray, CT, MR imaging, etc. The term imaging also includes practicing the technique on a patient.

Other features and advantages of the invention will be apparent from the following description of the preferred embodiments in conjunction with the claims and the drawings.

Brief Description of the Drawing

Figs. 1a and 1b are schematic diagrams of a hydrogel consisting of a backbone, a cross-linking agent, and at least one label. FIG. 1a shows an entrapped label, whereas FIG. 1b shows a covalently bound label.

Description of the Preferred Embodiments

Figure 1A:
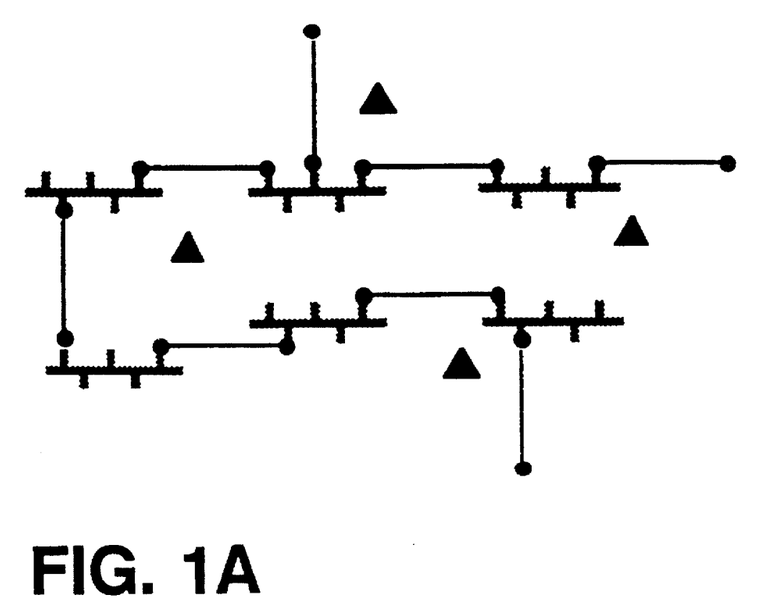
Figure 1B:
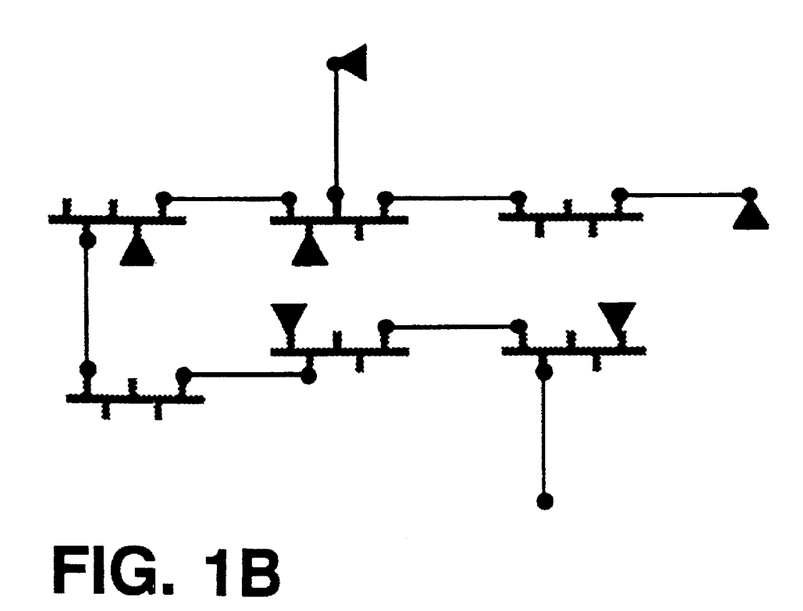

As shown in FIG. 1, the hydrogel compositions include a backbone (shown as ⊥⌐⊥⌐⊥) a cross-linking agent (shown as ● —572 ), and at least one reporter group, e.g., a label (shown as ▲). The preferred components are described separately below.

Backbone

The hydrogel composition includes any one of a variety of biocompatible, degradable, and metabolizable organic or inorganic backbones. The backbone is preferably a hydrophilic macromolecule with multiple side groups available to react with the cross-linking agent.

The concentration of the backbone in an initial reaction solution (backbone solubilized in water) has to be sufficiently high to allow extensive cross-linking and subsequent hydrogel formation. If the concentration of the backbone is too low, no hydrogel will form, although cross-linking may still occur to some extent.

Minimum concentrations for protein-based backbones are typically at least 5.0% protein by weight in the reaction solution, i.e., solubilized in 95% water, but may vary for different backbones. Preferred protein hydrogels contain 20–50% protein in the initial solution.

Minimum concentrations for polysaccharide backbones also depend on the structure and molecular weight of the specific backbone, but for carboxylated polysaccharides, starting solutions should be at least 1.0% of the polysaccharide. Preferred polysaccharide hydrogels contain 2–5% polysaccharide by weight in the initial solution.

The following list summarizes backbones suitable for use in the present invention:

Proteinaceous backbones
  Individual proteins
    albumins
    globulins
    extracellular matrix proteins (e.g. collagen, fibronectin)
    fibrinogen
    fibrin
    thrombin
  Plasma protein mixtures
    plasma
    plasma fractions
  Glycoproteins
  Chemically modified proteins
  Recombinant proteins or peptides

Sugar containing backbones
Carboxylated polysaccharides
  polymannuronic acid
  polygalacturonic acid
  polyguluronic acid
Aminated polysaccharides
  glycosaminoglycans
Activated polysaccharides
  dextran derivatives
  starch derivatives
Synthetic backbones
Polylysines
Polyethyleneimines
Polyethylene glycol and its derivatives The term "chemically modified protein" means a protein molecule in which at least one chemical bond is produced or eliminated within the molecule. The term includes proteins which are, e.g., acylated, glycosylated, deglycosylated, oxidized, reduced, fractionated into peptide fragments, or phosphorylated.

The most preferred backbones are albumin or carboxylated polysaccharides, e.g., polymannuronic or polygalacturonic acids, because of their degradation in vivo, known tissue compatibility, and relatively low cost.

Cross-linking Agents

As shown in FIG. 1, the cross-linking agents form covalent bonds with either two backbones, one backbone, or one backbone and a reporter group. The generic formula of a hydrophilic cross-linking agent for use in the hydrogel compositions of the invention is:

$$R_1-O-[(CH_2)_n-O]_m-R_2$$

Wherein each $R_1$ and $R_2$, independently, is an organic group, at least one of $R_1$ and $R_2$ being capable of reacting with said backbone, n is 2 or 3, inclusive, and m is an integer from 10 to 200, inclusive. $R_1$ and $R_2$ can be the same or different organic groups. Preferably n is 2, and m is preferably from 50 to 150. These cross-linking agents are easily hydrated, decrease the toxicity of the backbone, and decrease the immunogenicity of the hydrogel compositions. The molecular structures of suitable $R_1$ and $R_2$ groups are apparent from the following list of cross-linking agents.

Preferred cross-linking agents for use in the hydrogel compositions are highly reactive, polyvalent derivatives of polyalkylene glycol (PAG). For example, when n is 2, PAG is polyethylene glycol; when n is 3, PAG is polypropylene gycol. The cross-linking agents also include copolymers of PAG, e.g., polyethylene glycol/polypropylene glycol block copolymers ("Pluronics"). As used herein, the term "polyvalent" means that the agent has two or more reactive organic groups to bind to the side groups of the hydrogel backbone, i.e., $R_1$ and $R_2$.

The most preferred cross-linking agents are derivatives of polyethylene glycol (PEG). PEG itself is not a preferred cross-linking agent, because it will not readily react with the backbones.

Cross-linking agents suitable for use in the hydrogel compositions are summarized in the following list:
  Polyethylene or polyoxyethylene glycol derivatives
  bis-hydroxysuccinimide ester of PEG diacid
  bis-hydroxysulfosuccinimide ester of PEG diacid
  bis-imidate of PEG diacid
  bis-imidazolide of PEG diacid
  bis-imidazolide of PEG
  bis-halide (Cl, Br, F) of PEG
  bis-chloranhydride of PEG diacid
  bis (n-amino alkyl) of PEG
  bis (polyoxyethylene-bis[n-amino-alkyl])
  bis benzoxazolide of PEG
  Polyalkylene glycol derivatives
  bis-hydroxysuccinimide ester of PAG diacid
  bis-hydroxysulfosuccinimide ester of PAG diacid
  bis-imidate of PAG diacid
  bis-imidazolide of PAG diacid
  bis-imidazolide of PAG
  bis-halide (Cl, Br, F) of PAG
  bis-chloranhydride of PAG diacid
  bis (n-amino alkyl) of PAG
  bis (polyoxyalkylene-bis[n-amino-alkyl])
  bis benzoxazolide of PAG Diagnostic Labels The hydrogel compositions may be loaded with a diagnostic label either during synthesis of the hydrogel, or afterwards, e.g., by diffusion into the stable hydrogel composition. These labels either may be entrapped in the hydrogel matrix without any chemical bond, or they may be bonded, non-covalently or covalently, to the backbone or cross-linking agent of the hydrogel.

The release kinetics of the label are ultimately determined by the type of binding of the label and this invention covers the use of different release kinetics for different applications. For example, if fast release of a label is desired it should be non-covalently entrapped; when slow release is desired, e.g., when more toxic labels are used, the label should be covalently bonded.

The following list summarizes diagnostic labels suitable for loading into the hydrogel compositions. This list is exemplary, and any variety of diagnostic label could be used. As used herein, DTPA is diethylene triaminepentaacetic acid; DOTA is 1,4,7,10-tetraazacyclododecane-N,N,N',N'''-tetraacetic acid; EDTA is ethylenediaminetetraacetic acid; DO3A is 1,4,7,10-tetraazacyclododecane-N,N',N''-triacetic acid; NOTA is 1,4,7-triazacyclononane-N,N',N''-triacetic acid; TETA is 1,4,8,11-tetraazacyclotetradecane-N,N',N'', N'''-tetraacetic acid; and HBED is hydroxybenzylethylenediamine diacetic acid.

Radiopaque labels (for X-ray imaging)
  Inorganic and organic iodine compounds
    (e.g. diatrizoate, non-ionic dimers)
  Radiopaque metals and their salts
    (e.g. Ag, Au)
  Other radiopaque compounds
    (e.g. Ca salts, Ba salts)
Paramagnetic labels (for MR imaging)
  Gd-DTPA and its derivatives
    Gd-DTPA-protein
    Gd-DTPA-poly-L-lysine
    Gd-DTPA-dextran
    Gd-DTPA-polymers
  Other paramagnetic complexones
    Gd complexones
      (e.g. Gd-DOTA, Gd-EDTA, Gd-DO3A, Gd-NOTA, Gd-TETA)
    Mn complexones
      (e.g. Mn-DPDP )
    Fe complexones
      (e.g. Fe-HBED)
    Dy complexones
    Cu complexones Eu complexones
Er complexones
Cr complexones
Ni complexones
Co complexones
Superparamagnetic labels (for MR imaging)
Magnetites
Superparamagnetic iron oxides
Monocrystalline iron oxides
Other (for MR imaging)
Spin-labels
 (e.g. nitroxyl labels)

"Complexones" are chelates of metal ions with paramagnetic properties, but greatly reduced toxicity when compared to the free metal ions.

The amount of label to be loaded into the hydrogel depends on the nature of the label. For gadolinium containing compounds, about 15 mg of Gd-DTPA-BSA/ml of hydrogel have been found to provide a clear MR image. For iodinated compounds, e.g., Hypaque™, about 100 to 400 mg of iodine/ml of hydrogel have been found to provide a clear X-ray image.

Therapeutic Drugs

A variety of therapeutic drugs also may be loaded into the hydrogel compositions of the invention, either in addition to a diagnostic label, or in place of such a label. The drugs may be loaded into the hydrogel compositions in the same way as described above for the diagnostic labels, i.e., by entrapment or chemical bonding. The following list of therapeutic drugs is exemplary, but is not intended to be exhaustive:

Chemotherapeutic agents

Antibiotic agents

Cardiovascular agents

Analgesics, CNS drugs

Drugs affecting hematopoiesis and hemostasis

Hormones, prohormones

Proteins (including albumin)

Enzymes

Cells producing therapeutic agents (e.g. insulin)

Solutes (glucose, NaCl, etc)

The rate of release, or release kinetics, of these drugs from the hydrogel compositions once administered to a patient are a determined by a variety of factors including the size of the drug molecules, the specific backbone and cross-linking agents used to prepare the hydrogel, and the type of binding of the drug. This invention covers the use of different drug release kinetics for different applications. For example, to achieve plasma saturation quickly, a drug may be entrapped (see Example 4, below). If slower drug release is required, covalent bonding is preferred (see Example 2, below).

The amount of drug to be loaded into the hydrogel depends on the nature of the drug. For a chemotherapeutic drug, e.g., doxorubicin, and antibiotics, e.g., gentamicin, about 10 mg of the drug/ml of hydrogel have been found to be effective. The drug loaded hydrogels are administered to patients via a catheter in amounts ranging from about 0.1 to 00 ml of the hydrogel, preferably 2 to 10 ml.

Biological effects

Figure 2A:
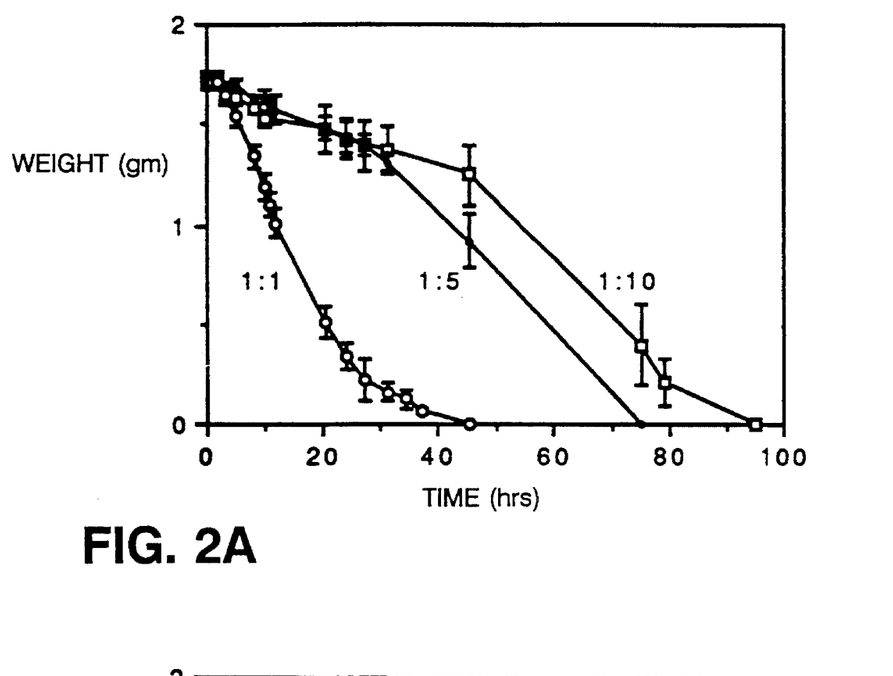
FIGS. 2a–c are graphs showing the degradation of hydrogel compositions of the invention under varying conditions.

The biological effects of the hydrogel compositions in a patient depend on the manner of administration, e.g. intravascular, implantation, or intracavitary, and the type of reporter group, e.g., label or drug, incorporated into the composition. Implanted hydrogel compositions are degraded in vivo (FIG. 2a–c) and in vitro when incubated with macrophages (not shown). In either case, as the hydrogel composition is degraded, it releases the loaded reporter group at a predetermined rate based on the known rate of degradation. These observations are confirmed by experiments which show that the preferred hydrogel compositions are degraded by proteases, such as trypsin (FIG. 2a). The degradation is a function of the amount of cross-linkage, the concentration of the backbone (see below), and the activity of the proteases.

Initial data suggest that degradation is a process which proceeds from the surface of the hydrogel particles. Cleaved fragments are presumed to be eliminated by the kidneys as is known to occur for PEG fragments with molecular weights of 4,000 daltons. In addition, the reporter group may be released from the hydrogel over time even if the hydrogel is not degraded.

The tissue response to implanted hydrogel compositions at the implantation sites is mild, i.e., less than that described by other investigators for wound dressings, e.g., Yoshioka, et al., *Int. J. Pharm.*, 8:131–141 (1981). When the preferred hydrogel compositions are administered intravascularly, the protective effects of PEG derivatives are believed to elicit only a minimal, if any, immunogenic response.

Use of the Hydrogel Compositions

The hydrogel compositions have a variety of medical and biomedical applications. The applications and usages are described briefly below and are discussed in more detail in the following specific examples.

The compositions may be used for intravascular embolization while imaging or for chemo-embolization; for drug delivery, e.g., antibiotic delivery during abscess drainages, slow release of chemotherapeutic drugs, pro-drug or enzyme delivery, and hormone replacement therapy; for estimating drug delivery by imaging based on the correlational dependence of the release of a therapeutic drug and the release of a diagnostic label; for MR imaging markers without magnetic distortion, e.g., surface skin markers or intracorporal markers for radiotherapy; for coating medical devices, e.g., as a lubricious coating for catheter systems, to improve the biocompatibility of interventional devices, and to visualize interventional devices with imaging techniques; for forming biodegradable devices for interventional use and implantation, e.g., a biodegradable vena cava filter with and without diagnostic labels, or a biodegradable substrate for stent or catheter synthesis; for immobilizing cells in the hydrogels for injection or implantation into a patient and imaging; and as a contrast agent for intravascular use.

EXAMPLES

1. Synthesis of a Bivalent Cross-linking Agent

Described here is the synthesis of bis(N-hydroxy-succinimidyl)polyethylene glycol disuccinate. This activated cross-linking agent is capable of reacting with amino groups of a suitable backbone.

Preparation of PEG-3350-disuccinate 60 g (17.9 mmol) of PEG-3,350 (Sigma Chemical Co, St. Louis, Mo.) was dissolved in 300 ml of dioxane in a 2-necked 1 L flask and heated to 90° C. 18 g of succinic anhydride (5-fold molar excess) and 0.5 g of N,N'-dimethylaminopyridine were dissolved in the same solution. The flask was equipped with a refluxing column and inlet for nitrogen. The mixture was slowly purged with nitrogen and heated to 100° C. for 8 hours. The mixture was cooled, concentrated three-fold by rotary evaporation, filtered on a glass-fritted filter (20–30 μm) to remove succinic acid, and evaporated to dryness. The residue was dissolved in a minimal amount of ethylacetate (50 ml) and added to 300 ml of ethyl ether. A precipitate formed at 4° C. and was separated, and the procedure was repeated. The thus purified precipitate was dissolved in 100 ml of water and passed through a column containing 25 g of AG 50W-X8 resin (Bio-Rad, Melville, N.Y). The flow-through was diluted 5-fold with water and lyophilized. The yield was 50 g PEG-3350-disuccinate, or about 78%.

Synthesis of bis-hydroxysuccinimide ester of PEG disuccinate 30 g of the dry solid PEG-3350-disuccinate from the previous step was dissolved in 100 ml of tetrahydrofuran and added to 4 g of N-hydroxysuccinimide (2-fold molar excess). After solubilization, 3.8 g (1.1 molar excess) of dicyclohexycarbodiimide was added, the solution was stirred for 3 hours, cooled to 4° C., and filtered at room temperature to remove insoluble dicyclohexylurea. The filtrate was evaporated to dryness by rotary evaporation, re-dissolved in a minimal amount of methanol (20 ml) and filtered again. Then 300 ml of diethyl ether was added and the precipitate was collected by filtration. This procedure was repeated once. The yield was 23 g of bis-hydroxysuccinimide ester of PEG disuccinate, or about 72%.

2. Synthesis of Paramagnetic Cross-linked Protein Hydrogel

Synthesis of Gd-DTPA-albumin

Gd-DTPA was attached to bovine serum albumin (BSA) using a method similar to those previously described in Frejcarek et al., *Biochem. Biophys. Res. Comm.*, 77:581–586 (1977) and Hnatowich et al., *J. Immunol. Meth.*, 65:147–157 (1983). Briefly, 2 g of BSA (Sigma) were dissolved in 100 ml of bicarbonate buffer at pH 9.1, and an aliquot of cyclic DTPA anhydride ("cDTPAA") (Pierce) was added. After two hours, free DTPA was removed by ultrafiltration with a YM3 filter (Amicon, Beverly, Mass.). Transchelation of BSA-DTPA was performed with 0.1M gadolinium citrate. The reaction product, Gd-DTPA-BSA, was purified by further ultrafiltration, and then lyophilized.

Formation of a paramagnetic hydrogel 1400 mg BSA and 10 mg of Gd-DTPA-BSA were dissolved in 7 ml of phosphate buffered normal saline (pH 8.5). Then 460 mg of the cross-linking agent bis-hydroxysuccinimide ester of PEG disuccinate (Example 1) was dissolved in 600 µl DMSO at 60° C. The cross-linking agent was mixed with the BSA solution and reacted at room temperature for 15 minutes during which gelation occurred. Thereafter, the hydrogel composition was removed and washed in 6 L of 0.9% NaCl for 24 hours to remove DMSO and unreacted products. As an alternative to BSA, equivalent amounts of human blood or human IgG were also used for cross-linking.

Formation of paramagnetic hydrogel with a therapeutic drug

Five ml of a 20% BSA/Gd-DTPA-BSA solution was prepared as described above. One µg of rhodamine X (as a model of a therapeutic drug) (Molecular Probes, Oregon) in 20 µl DMSO was added to an 2.5 ml aliquot of this solution. One mg of doxorubicin was added to the other 2.5 ml aliquot. Both samples were then mixed with 230 mg of the cross-linking agent dissolved in 300 µl DMSO, each at 60° C. After reaction at room temperature for 15 minutes, paramagnetic hydrogels with the therapeutic drug models were removed and washed in 6 L of 0.9% NaCl for 24 hours to remove DMSO and unreacted products. This material is preferred for embolization.

3. Synthesis of Paramagnetic Cross-linked Polysaccharide Hydrogel

A polysaccharide-based hydrogel cross-linked with a bivalent PEG derivative was synthesized as follows. A 4% sodium alginate (Sigma) solution was prepared and its pH adjusted to 5.0 using 1N HCl. 100 mg of 15 mM of N-hydroxysulfosuccinimide (Pierce) was added while re-adjusting the pH to 5.0 to activate available carboxyl groups on the polymannuronic acid backbone. 100 mg of 1-ethyl-3-(dimethyl-aminopropyl)carbodiimide hydrochloride was dissolved in 100 µl $H_2O$ and added to the above solution. The mixture was allowed to react for 10 minutes at room temperature. The pH of the solution was then raised to 8.5 with 5N NaOH and 100 µl of concentrated polyoxyethylene-bis (6-aminohexyl) (Sigma) or bis(polyoxyethylene-bis 3-amino-2-hydroxy-propyl) was added. After gelation, the hydrogel was dialyzed in 0.9% NaCl to remove by-products of the reaction.

4. Synthesis of Radiopaque Cross-linked Hydrogel

Two ml of BSA (40% with 10 mg of Gd-DTPA-BSA) was mixed with 2 ml of aqueous sodium diatrizoate 76%, which contains approximately 37% organically bound iodine. The pH was adjusted to 8.5 with bicarbonate, and reacted with 200 mg cross-linking agent in 200 µl DMSO. The hydrogel was then implanted into a rat. No adverse side effects were observed.

5. Degradation of Paramagnetic Hydrogel

Figure 2B:
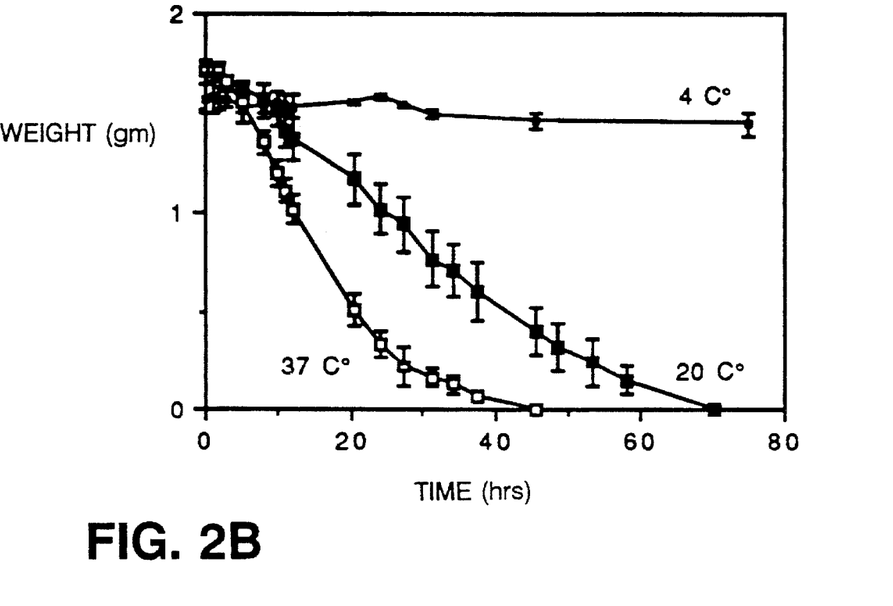
Figure 2C:
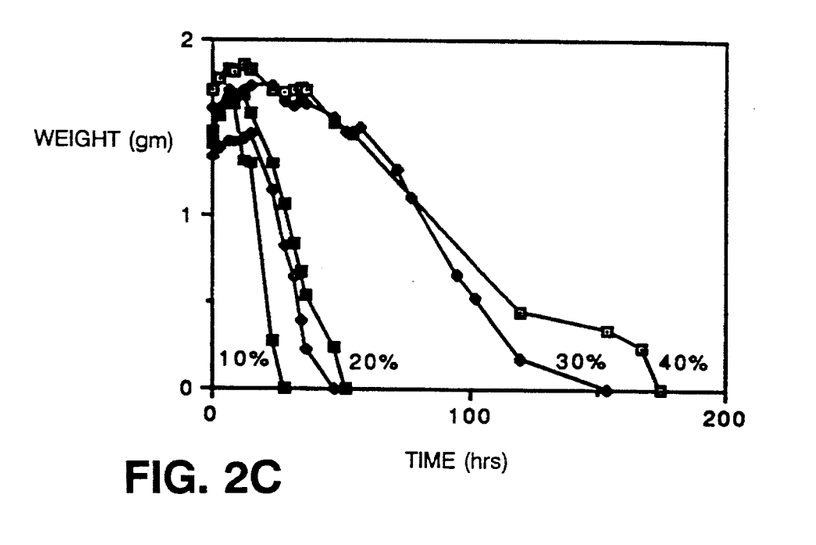

Hydrogels with different concentrations of albumin backbone (40%, 30%, 20%, 15%, 10%) were synthesized as described in Example 2. Equivalent amounts of the hydrogel samples were then incubated at different concentrations of trypsin (0.05% =1:1, 1:5, 1:10) (FIG. 2a), and at different temperatures (37° C., 20° C. 4° C.) (FIG. 2b), to determine the degradation of the hydrogel. These experiments unequivocally demonstrate that degradation occurs in vitro and that this degradation is dependent on the activity of the protease. As shown in FIG. 2a, the highest concentration of trypsin (1:1) caused the fastest degradation. FIG. 2b shows that degradation increases with temperature. Finally, FIG. 2c shows that degradation is fastest with the lowest concentration (10%) of the albumin backbone in the hydrogel composition.

6. Correlational Estimation of Drug Concentration

The following experiments were conducted to show that drug release kinetics from the hydrogel can be calculated by knowing the release kinetics of diagnostic, e.g., radiographic, labels. The hydrogels used in these experiments were similar to those described in Example 2.

Covalent drug bonding

Figure 3:
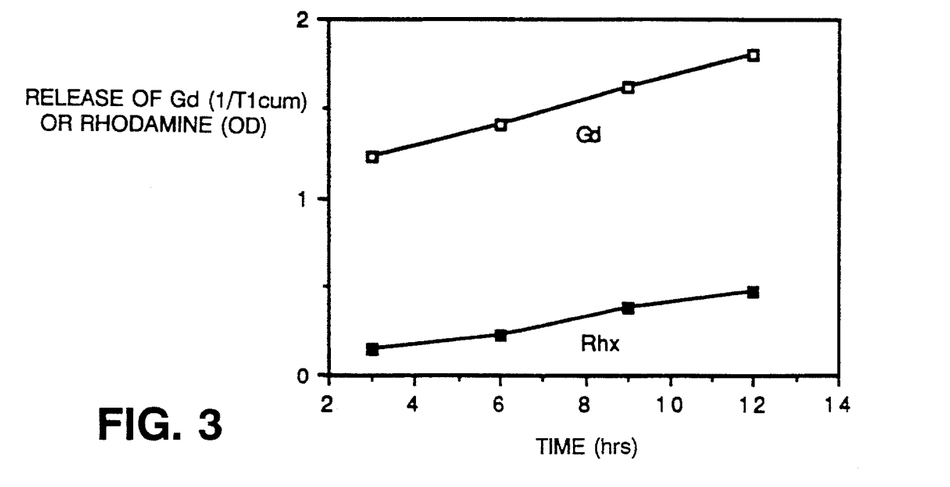
FIG. 3 is a graph showing the release of gadolinium and rhodamine (covalently bonded) from a hydrogel composition in an in vitro system.

The hydrogel compositions contained Gd-DTPA (diagnostic T1 label) and rhodamine (drug model) covalently bound to an albumin backbone. The hydrogels were extensively washed in saline to remove unbound labels and then incubated with trypsin (0.05%) at 37° C. Release of Gd (shown by □) and rhodamine (Rhx)(shown by ■) was determined by T1 and optical density measurements. FIG. 3 compares Gd release and rhodamine release within the first 12 hours after incubation showing excellent correlation.

Non-covalent drug binding

Figure 4:
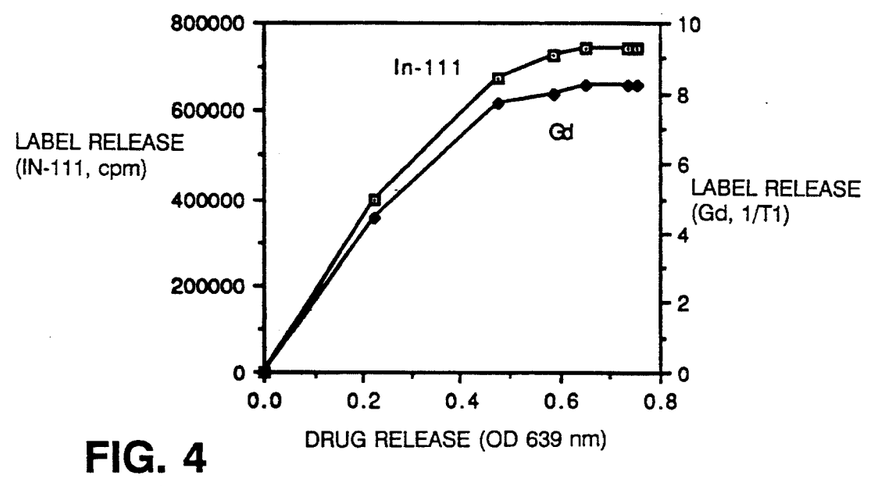
FIG. 4 is a graph showing the release of gadolinium and 111-Indium (both non-covalently bonded) from a hydrogel composition in an in vitro system.

In this set of experiments, hydrogel compositions were prepared as described in Example 2, and T1 label (Gd-DTPA), radioactive label (111-In-DTPA), and isosulfan blue (therapeutic drug model), were entrapped non-covalently in the hydrogel during synthesis. The gels were subsequently incubated in normal saline. Then T1 measurements, radioactivity measurements, and OD measurements of the supernatant were obtained at various time intervals. The graph in FIG. 4 summarizes the results.

These data indicate that there is an excellent correlation between the release of the model therapeutic drug (isosulfan blue) and the diagnostic labels (111-In or Gd). The release of either of the three compounds is virtually identical in hydrogels of different densities. For example, the best polynomial fit for two different gels are:

20% gel: $f(x)=24.36x-17.87x2$; $r2=0.999$

40% gel: $f(x)=24.28x-17.11x2$; $r2=0.996$

Figure 5:
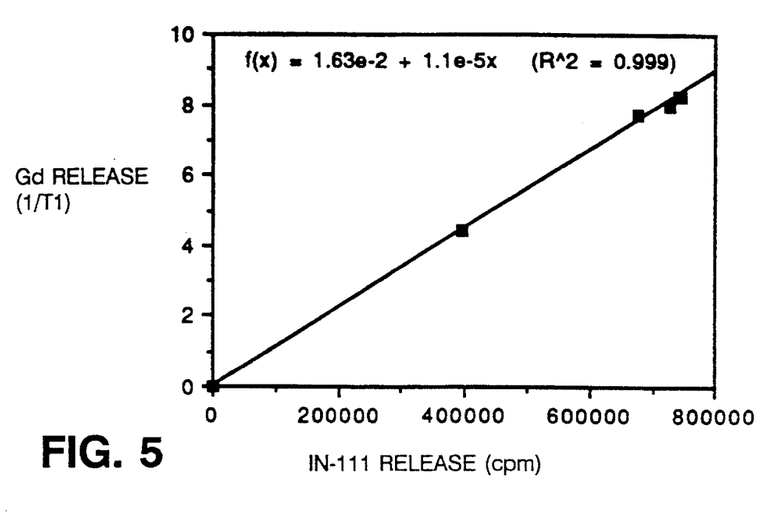
FIG. 5 is a graph showing the correlation between the release of 111-In-DTPA and Gd-DTPA from a hydrogel composition in vitro.

As shown in FIG. 5, the correlation between release of 111-In-DTPA and Gd-DTPA from the hydrogel is virtually identical. From knowing one concentration, the concentration of the other label can be mathematically estimated by imaging without additional physical measurements.

Drug release over time

Figure 6:
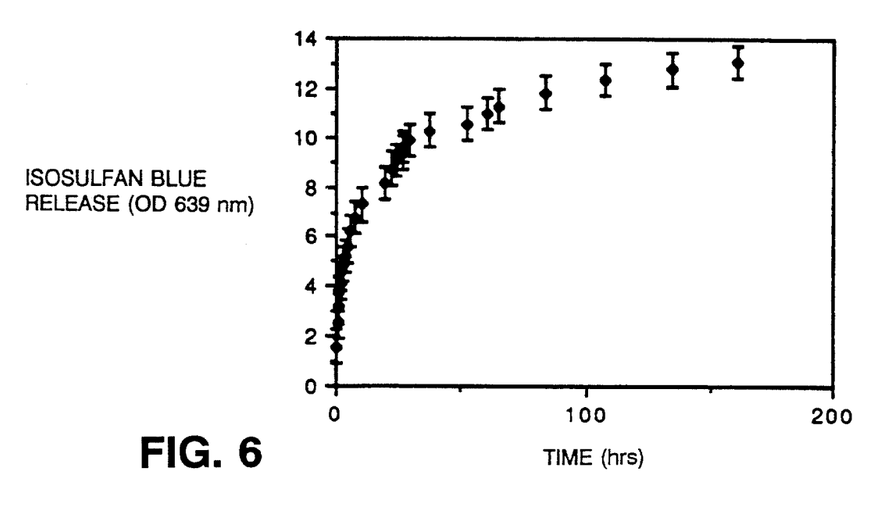
FIG. 6 is a graph showing the release of a therapeutic drug model (isosulfan blue) from a hydrogel composition (non-covalently bonded) in an in vitro system.

The following experiment demonstrates the release of a non-covalently entrapped drug (modeled by isosulfan blue) from a 1 ml hydrogel sample. FIG. 6 shows the exponential release of the compound.

7. MR Imaging

Figure 7:
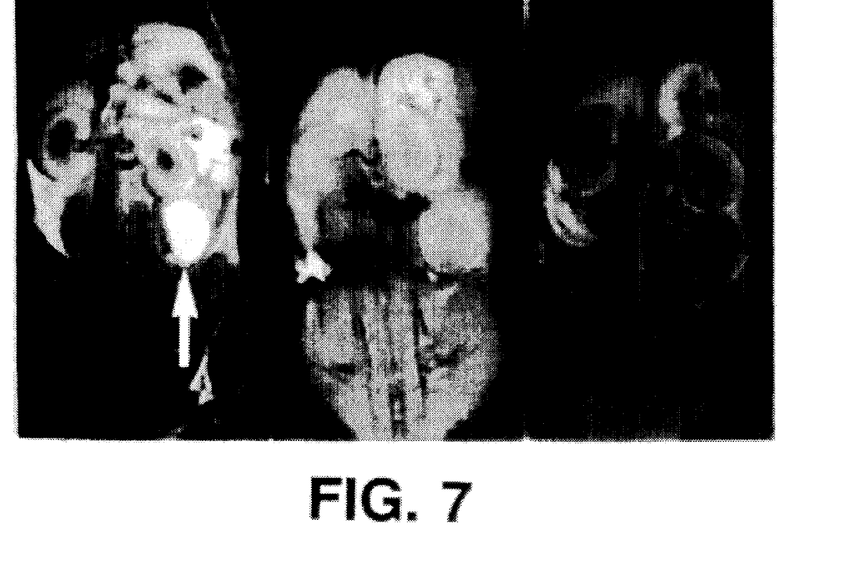
FIG. 7 is a series of MR images taken at (from left to right) 2, 5, and 10 days, of a rat implanted with a hydrogel disk (arrow), showing the release of a label over time.

The following experiments were performed to determine the degradation of hydrogels after surgical implantation into rats. Briefly, paramagnetic 0.5 ml hydrogels prepared as described in Example 2 were implanted into the left para-renal muscle groups (n=4), into the peritoneum (n=2), or subcutaneously (n=2) in rats (200 g CD, Charles River Breeders). The dissolution of these gels, which contained covalently bonded Gd-DTPA, could be observed over time by repeated MR imaging (1.5 T GE Medical Systems, SE 300/20). These studies show that peritoneally implanted samples degraded faster (4 days) than intramuscularly implanted samples (6 days). This is likely to be related to the higher concentration of peritoneal macrophages, capable of releasing proteases that enzymatically degrade the preferred hydrogels. FIG. 7 shows the dissolution of an implanted hydrogel button in a rat at 2, 5, and 10 days after implantation (from left to right).

8. Embolization

The following embolization experiment was designed to demonstrate that the preferred hydrogel compositions of this invention can be passed through interventional catheter systems, and that these hydrogels are suitable for intravascular embolization of tumors or organs.

A 2.5 kg New Zealand White rabbit was implanted with VX2 tumor cells in the flank. Several weeks after implantation the tumor had grown to a 5 cm solid mass infiltrating the retro-peritoneum. A right femoral artery cut-down was performed and a 3 Fr catheter was introduced and advanced into the aorta under fluoroscopic guidance (Fischer Imaging Systems). After injection of an iodinated contrast agent, feeding tumor vessels could be demonstrated to arise from the aorta. One of these vessels was cannulated and 0.2 ml of finely minced hydrogel beads (50–300 μm) were administered into that tumor vessel. Subsequent fluoroscopy demonstrated complete occlusion of the tumor vessel by the hydrogel.

Figure 8:
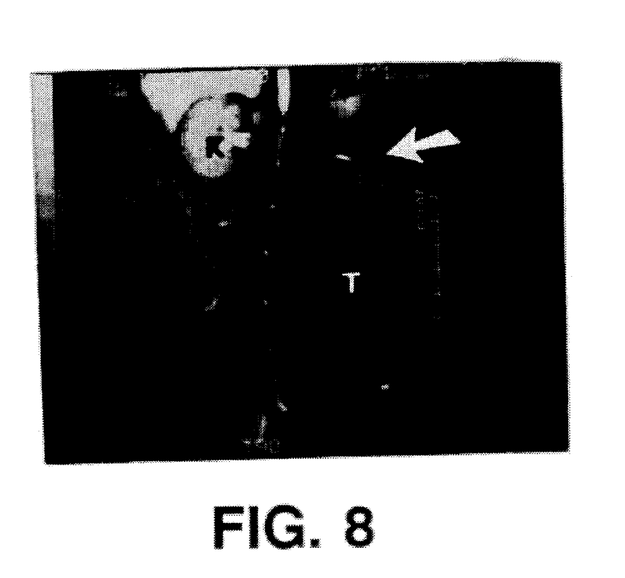
FIG. 8 is a photo of the left kidney (arrow) and tumor of a rabbit which are embolized with a hydrogel composition of the invention.

In addition to the above experiment, the left renal artery was cannulated and 1 ml of hydrogel was administered. Complete occlusion of the renal artery and nonperfusion of the left kidney was demonstrated by subsequent MR angiography (1.5 T GE Imaging system, 3D-TOF sequence). FIG. 8 shows the results of this embolization procedure. The normally perfused right kidney (K) appears perfused (bright) after I.V. administration of a T1 agent whereas the left embolized kidney appears non-perfused (black).

9. Chemotherapeutic Drug Binding to Paramagnetic Hydrogel

A 40% solution of BSA with 10 mg BSA-Gd-DTPA in 0.1M carbonate buffer was prepared and the pH was adjusted to 8.5. 2 mg of doxorubicin (2 mg/ml; VHA plus) was added to this solution and the pH was adjusted with 0.05M HEPES buffer. 200 mg of cross-linking agent (see Example 1) was added and dissolved in 200 μl of DMSO. The sample was cross-linked at room temperature for 2 hours and then dialyzed in 0.9% NaCl for 24 hours. Binding of doxorubicin to the hydrogel matrix was greater than 95%.

10. Color coding

To easily recognize an entrapped or covalently bonded reporter group within a hydrogel, a chromophore, or mixtures of chromophores, may be added to the hydrogel during synthesis. A variety of chromophores are suitable including, e.g., indocyanine green, fluorescein, rhodamine, rose bengal, gentian violet, methylene blue, isosulfan blue, and other reactive colors (Sigma).

In the following example, a Gd-DTPA containing hydrogel was synthesized as described in Example 2. Briefly, a solution containing BSA and BSA-Gd-DTPA was reacted with 10 μl of DMSO to which had been added 5 μg of rhodamine X (Molecular Probes, Oregon). The solutions were reacted at room temperature for 15 minutes, cross-linked with activated PEG, and then washed to remove free rhodamine.

11. Lyophilization

Hydrogel prepared as described in Example 2 was subjected to lyophilization (Vitis Freezemobile) by first freezing the sample in liquid nitrogen. Lyophilized hydrogel samples were stored for two months and reconstituted with water to yield a hydrogel with properties similar in appearance, density and magnetic properties, to that of the non-lyophilized hydrogel.

12. Use of the Hydrogels as Contrast Agents Without Embolization

The hydrogel composition described in Example 2 was finely homogenized (Brinkman Polytron, Wheaton tissue homogenizer, Branson sonifier) to obtain an average particle size of below 100 nm. The size of the particles was controlled by passing the solution successively through 0.45 and 0.1 μm filters (Acrodisk). After concentration by centrifugation, 1 ml of the suspension was administered intravenously to a rat. Because the individual particles are too small to occlude capillaries, no embolization occurred and the animal survived the injection.

13. Coating of Interventional Devices with Paramagnetic Hydrogel

In the following experiment, an angiographic catheter was coated with a paramagnetic hydrogel for improved delineation by MR imaging. The surface of a 3 Fr angiographic catheter was cleaned with glass wool and ether. A section of the catheter was then submerged in a 20% BSA-(Gd-DTPA)

solution (200 µl). The albumin adhered to the catheter non-specifically. The catheter was then dried at room temperature and subsequently immersed in 50 µg of DMSO solution containing the hydroxysuccinimide ester of PEG-bissuccinate of Example 1 to cross-link the albumin on the catheter. The catheter was then washed in saline and is ready for MR imaging.

14. Hydrogel Matrix for Cell Support

Living cells may be loaded into the hydrogel compositions and propagated to produce therapeutic agents. Such cells would have low or non-existent toxicity. For example, cells with the capacity to secrete therapeutic agents, e.g., insulin or other hormones, enzymes, or proteins, can be loaded into a hydrogel and implanted into a patient. If an appropriate label is also loaded into this hydrogel, an MR image will indicate cell density and activity, and/or the presence or concentration of the therapeutic agents, in the hydrogel.

To prepare such a hydrogel composition, the desired cells are dispersed, e.g., by vortexing, in a sterile solution of 10% serum, e.g., fetal calf, bovine, or human, in Dulbecco's modified Eagle medium at a pH of 7.9. At this stage, suitable therapeutic drugs and/or diagnostic labels as described above may be added. The number of cells loaded into the hydrogel is selected to achieve a specific dosage of the therapeutic agent secreted by the cells per day. For example, if the cells are secreting insulin, the standard dosage is about 10 to 80 I.U./day. This mixture is cross-linked by adding a cross-linking agent, e.g., the bis(N-hydroxy-succinimidyl)polyethylene glycol disuccinate described in Example 1, which is dissolved in DMSO. The cell loaded hydrogel is kept in tissue culture medium for a time sufficient to remove any DMSO or other contaminants, e.g., 12 to 24 hours, before implantation into a patient.

Other Embodiments

It is to be understood that while the invention has been described in conjunction with the preferred embodiments thereof, that the foregoing description is intended to illustrate and not limit the scope of the invention, which is defined by the scope of the appended claims. Other aspects, advantages, and modifications within the scope of the invention will be apparent to those skilled in the art to which the invention pertains.

What is claimed is:

1. A biocompatible, biodegradable, hydrogel comprising a backbone bonded to a cross-linking agent, wherein said cross-linking agent is a bis-hydroxysuccinimide ester of polyalkylene glycol ("PAG") diacid, bis-hydroxysulfosuccinimide ester of PAG diacid, bis-imidate of PAG diacid, bis-imidazolide of PAG diacid, bis-imidazolide of PAG, bis-halide of PAG, bis-chloranhydride of PAG diacid, bis (n-amino alkyl) of PAG, bis (polyoxyalkylene-bis, or bis benzoxazolide of PAG.

2. The hydrogel of claim 1, further comprising a reporter group loaded into said hydrogel.

3. The hydrogel of claim 2, wherein said reporter group comprises a diagnostic label.

4. The hydrogel of claim 3, wherein said label is detectable by X-ray or magnetic resonance imaging.

5. The hydrogel of claim 4, wherein said X-ray detectable label is an iodine containing compound.

6. The hydrogel of claim 4, wherein said magnetic resonance imaging detectable label is a gadolinium containing compound.

7. The hydrogel of claim 6, wherein said label is gadolinium-diethylenetriamine-pentaacetic acid.

8. The hydrogel of claim 2, wherein said reporter group is entrapped in said hydrogel.

9. The hydrogel of claim 1, wherein said backbone comprises a proteinaceous macromolecule.

10. The hydrogel of claim 9, wherein said backbone comprises from 5 to 50 percent protein by weight of an initial proteinaceous solution.

11. The hydrogel of claim 10, wherein said backbone comprises from 20 to 50 percent protein by weight of said initial solution.

12. The hydrogel of claim 1, herein said backbone is a plasma protein, glycoprotein, polyamino acid homopolymer, polysaccharide derivative, glycosaminoglycan, polyethyleneamine, or polyethylene glycol derivative.

13. The hydrogel of claim 12, wherein said backbone is albumin, polymannuronic acid, or polygalacturonic acid.

14. The hydrogel of claim 12, wherein said polysaccharide derivative is a dextran or starch derivative.

15. The hydrogel of claim 1, wherein said backbone is a recombinant protein.

16. The hydrogel of claim 1, wherein said cross-linking agent is a bis-hydroxysuccinimide ester of polyethylene glycol ("PEG") diacid, bis-hydroxysulfosuccinimide ester of PEG diacid, bis-imidate of PEG diacid, bis-imidazolide of PEG diacid, bis-imidazolide of PEG, bis-halide of PEG, bis-chloranhydride of PEG diacid, bis (n-amino alkyl) of PEG, bis (polyoxyethylene-bis ), or bis benzoxazolide of PEG.

17. A therapeutic composition comprising a biocompatible, biodegradable hydrogel comprising a backbone bonded to a cross-linking agent, wherein said cross-linking agent is a bis-hydroxysuccinimide ester of polyalkylene glycol ("PAG") diacid, bis-hydroxysulfosuccinimide ester of PAG diacid, bis-imidate of PAG diacid, bis-imidazolide of PAG diacid, bis-imidazolide of PAG, bis-halide of PAG, bis-chloranhydride of PAG diacid, bis (n-amino alkyl) of PAG, bis (polyoxyalkylene-bis), or bis benzoxazolide of PAG, a diagnostic label, and a therapeutic drug, wherein said diagnostic label and said therapeutic drug are both loaded into said hydrogel.

\* \* \* \* \*

UNITED STATES PATENT AND TRADEMARK OFFICE
CERTIFICATEOF CORRECTION

PATENT NO. : 5,514,379

DATED : May 7, 1996

INVENTOR(S) : Ralph Weissleder and Alexei Bogdanov

It is certified that error appears in the above-identified patent and that said Letters Patent is hereby corrected as shown below:

Column 6, line 25, replace "(shown as ●——— 572)" with
--(shown as ●———●)--;

Column 9, line 59, replace "00 ml" with --100 ml--;

Column 16, claim 12, line 23, replace "herein" with
--wherein--.

Signed and Sealed this

Tenth Day of September, 1996

BRUCE LEHMAN

*Attest:*

*Attesting Officer*          *Commissioner of Patents and Trademarks*